United States Patent
Parfenov et al.

(10) Patent No.: US 11,597,199 B2
(45) Date of Patent: Mar. 7, 2023

(54) TURNSTILE SYSTEM FOR TISSUE SPHEROID BIOPRINTING

(71) Applicant: VIVAX BIO, LLC, New York, NY (US)

(72) Inventors: Vladislav Parfenov, Podolsk (RU); Frederico David Alencar de Sena Pereira, Vitória da Conquista (BR); Yusef Khesuani, Moscow (RU); Vladimir Mironov, Moscow (RU); Elena Bulanova, Moscow (RU); Elizaveta Kudan, Moscow (RU); Alexander Ostrovskiy, Moscow (RU); Yakov Balakhovsky, New York, NY (US); Anastasiia Kniazeva, Talovskiy area (RU); Stanislav Petrov, Pushkino (RU)

(73) Assignee: VIVAX BIO, LLC, New York, NY (US)

( * ) Notice: Subject to any disclaimer, the term of this patent is extended or adjusted under 35 U.S.C. 154(b) by 656 days.

(21) Appl. No.: 16/677,879

(22) Filed: Nov. 8, 2019

(65) Prior Publication Data
US 2020/0164627 A1    May 28, 2020

Related U.S. Application Data

(60) Provisional application No. 62/892,084, filed on Aug. 27, 2019.

(30) Foreign Application Priority Data

Nov. 28, 2018    (RU) ................................ 2018141959

(51) Int. Cl.
B33Y 10/00    (2015.01)
B33Y 30/00    (2015.01)
(Continued)

(52) U.S. Cl.
CPC ............... *B33Y 10/00* (2014.12); *B33Y 30/00* (2014.12); *B33Y 70/00* (2014.12); *C12M 21/08* (2013.01);
(Continued)

(58) Field of Classification Search
CPC ......... B33Y 10/00; B33Y 30/00; B33Y 70/00; C12M 3/06; C12M 21/08; C12M 23/16;
(Continued)

(56) References Cited

U.S. PATENT DOCUMENTS

2008/0070304 A1* 3/2008 Forgacs ................. C12M 33/12
                                                    435/395
2015/0375453 A1* 12/2015 Yost ...................... B29C 64/393
                                                    435/174

* cited by examiner

*Primary Examiner* — Anh T Vo
(74) *Attorney, Agent, or Firm* — Epstein Drangel LLP; Robert L. Epstein

(57) ABSTRACT

A group of inventions relates to biotechnology. Disclosed are a printing head and a printing device with fabric spheroids. The printing head includes a system of channels containing input and output channels, upper and lower channels for separation of nutrient medium, as well as a channel for a supporting plunger. Inlet channel has diameter providing movement of spheroid on it only by one. Output channel has diameter not less than diameter of inlet channel, includes input hole for input of printing tool and outlet hole for output of spheroids. Separation channels are made with possibility of connection of nutrient removal device with outlet channel through system of microchannels. Device includes a printing head, a device for feeding spheroids with a nutrient medium into an inlet channel, a device for removal of nutrient medium, a supporting plunger, a printing tool, a system for recording position of the spheroid in the output channel and a computing device for control. Inventions provide higher accuracy of positioning of spheroid on (Continued)

printed surface, improved quality of production of three-dimensional structures and faster printing.

10 Claims, 3 Drawing Sheets

(51) Int. Cl.
*B33Y 70/00* (2020.01)
*C12M 3/06* (2006.01)
*C12N 5/00* (2006.01)
*C12M 3/00* (2006.01)
*C12N 5/071* (2010.01)

(52) U.S. Cl.
CPC ............ *C12M 23/16* (2013.01); *C12N 5/0062* (2013.01); *C12N 5/0602* (2013.01)

(58) Field of Classification Search
CPC .... C12M 33/00; C12N 5/0062; C12N 5/0602; C12N 5/071; C12N 2529/10
See application file for complete search history.

TURNSTILE SYSTEM FOR TISSUE SPHEROID BIOPRINTING

The group of inventions belongs to the field of biotechnology. A printhead and a fabric spheroid printing device are proposed. The printhead includes a channel system comprising input and output channels, upper and lower feed separation channels, and a channel for the backing plunger. The input channel has a diameter providing movement of a spheroid only on it. The output channel has a diameter not less than the diameter of the input channel, includes an input hole for the input of the printing tool and an output hole for the output of spheroids. The separation channels are made with the possibility of connection of the device for removal of the nutrient medium with the outlet channel via a system of microchannels. The device includes a print head, a device for supplying spheroids with a nutrient medium to the input channel, a device for removing the nutrient medium, a supporting plunger, a printing tool, a position registration system of the spheroid in the output channel and a computing device to control. The inventions provide an increase in the accuracy of positioning the spheroid on the printed surface, improving the quality of production of three-dimensional structures and increasing the printing speed. 2 n. and 8 z. p. f-les, 3 pic.

FIELD OF TECHNOLOGY TO WHICH THE INVENTION RELATES

This invention relates to the field of medicine and medical devices, in general, to three-dimensional (3D) printing and the creation of three-dimensional biological organ and tissue engineering constructs. In particular, the invention relates to the device and printhead of a tissue spheroidal printing device.

BACKGROUND OF THE INVENTION

In recent decades, the concept of using tissue spheroids as building blocks for bioprinting and biofabrication of organ and tissue engineering constructs has emerged. Tissue spheroids are tightly packed aggregates of cells that have signs of natural tissue morphology. Distinctive features of tissue spheroids are: (a) high packing density of cells in a spheroid; (b) the ability to merge tissues (closely adjacent tissue spheroids tend to merge into larger tissue structures). There is known a tissue spheroidal bioprinting device (Eurasian patent No. 028039 B1, class C12N 5/07, B33Y 10/00, B33Y 30/00, B33Y 70/00, A61F 2/02, published on 29 Sep. 2017)/This invention allows for the production of bioprinting with tissue spheroids using a nozzle in the form of a syringe device. Spheroids are loaded into the nozzle. However, using this method can lead to spheroids merging with each other in a syringe, the tube or the needle. This can cause the needle to clog and obstruct the passage of subsequent tissue spheroids, which can lead to damage and destruction of the spheroids during extrusion. Also, the known device does not guarantee extrusion of a single spheroid, and it can lead to false printing or printing of several spheroids instead of one.

There is one device (no. WO2012176751A1 of the class C12M33/04, published 27 Dec. 2012), which uses the method of bioprinting with single tissue spheroids by taking spheroids one-by-one out of a 96-hole plate with a non-adhesive bottom and threading them onto rods. This method allows printing with spheroids of at least 500 micrometers in size, which in turn limits the scope of application of the technology, as certain cell types are unable to form spheroids of that size. Moreover, spheroids of this diameter may have a central area with a minimum number of living cells. In addition, the spheroid may be destroyed by stringing on the rods, and the use of a rigid frame may have a negative impact on the merger of a certain type of spheroids due to the compressibility (deformation) of constructs in the process of merging during cultivation. The speed of bioprinting in this method is limited by the speed of movement of the nozzle to take spheroids out of the die and thread them onto the rods.

The closest analog of the proposed invention is the method and the device presented in the work of the group led by Tim B. F Woodfield: "Integrated System for 3D Assembly of Bio-scaffolds and Cells," Toronto, Ontario, Canada, Aug. 21-24, 2010. The device contains a spheroid supply system to the printhead that includes a channel into which the spheroids are loaded, a channel with an extruding piston installed, a channel with a blocking piston installed, and a single spheroid outlet channel. First, the blocking piston closes and blocks the channel into which the spheroid is moved from the loading channel as a result of a brief pressure surge. When the blocking piston is moved back, the squeezing piston goes into motion, and the spheroid enters the outlet channel. To control the plungers, solenoids controlled by controllers are used in accordance with the set algorithm. The mechanism of direct movement of a single spheroid on the printed surface (substrate) is not presented in this paper, and the diameter of spheroids in this paper was about 1300 micrometers. One spheroid is printed in a three-step process, the printing speed being dependent on the speed of these three steps. During printing, there is a possibility that nutrient medium is excessively formed on the receiving surface. This may prevent precise inclusion of individual tissue spheroids on the receiving surface or on one or more layers of tissue spheroids.

To improve bioprinting, it is advisable to avoid or minimize at least one or more of the above disadvantages.

REVELATION OF THE ESSENCE OF THE INVENTION

The purpose of the proposed invention is to improve the quality of bioprinting by providing bioprinting with single tissue spheroids without damaging them and without releasing the nutrient medium from the device onto the substrate, which allows increasing the accuracy of spheroid positioning on the printed surface and improving the quality of production of three-dimensional structures (tissue engineering constructs).

Another technical task to be solved by the proposed invention is increasing the speed of printing.

An additional technical task to be solved by the proposed invention is to provide bioprinting with tissue spheroids of optimal diameter (within a range of 290 to 400 micrometers) in terms of printing performance and viability of spheroids.

The above objectives are achieved by the following means, as set out below.

In the first aspect, a printhead is proposed for use in a tissue spheroidal printer with a channel system that includes:

at least one inlet channel of printhead (hereafter the inlet channel), which diameter is selected according to the diameter of the tissue spheroids used for printing so that the spheroids can only move one at a time through the channel, for receiving and directing the supply of nutrient medium with tissue spheroids toward the outlet channel of the printhead, an outlet channel of the printhead (hereinafter the outlet channel) which diameter is selected to be at least as large as the inlet channel diameter, with the top entrance port for the print tool and the bottom exit port for the output of tissue spheroids, the upper channel of separation of the nutrient medium and the lower channel of separation of the nutrient medium, each of which connects the device for removal of the nutrient medium to the output channel through a system of microchannels: accordingly, the upper separation channel of the nutrient medium is in the first region of the output channel, and the lower separation channel of the nutrient medium is in the second region of the output channel, a channel for the supporting piston, configured to insert supporting piston into the outlet channel.

The channels are configured in such a way that the diameter of all inlet channels is the same, the inlet channels are connected to the outlet channel at the first intersection point between the first area of the outlet channel and the second area of the outlet channel, and the supporting piston channel is connected to the outlet channel at the second intersection point between the first intersection point and the second area of the outlet channel, and the diameter of each microchannel of the microchannel system is selected depending on the diameter of the tissue spheroids used for printing so that spheroids could not move along the microchannel.

In some embodiments of the first aspect of the invention, one or more inlet channels, and in some embodiments, all inlet channels, have curvilinear form.

In some embodiments of the first aspect of the invention, the system of channels includes from 1 to 5, in the preferred embodiments, from 1 to 2, inlet channels.

In some embodiments of the first aspect of the invention, the channels are located inside the bulky body.

In some embodiments of the first aspect of the invention, the bulky body is made of solid, transparent material.

In some preferred embodiments of the first aspect of this invention, the diameter of tissue spheroids used is within the range of 290-400 µm, and the diameter of the inlet and outlet channels is by 30 µm±10 µm larger than the diameter of the used tissue spheroids.

In some preferred embodiments of the first aspect of this invention, the diameter of each microchannel is less than the diameter of the used tissue spheroids and is not to exceed 200 µm.

In some embodiments of the first aspect of the invention, the diameter of the microchannels ranges from 10 µm to 150 µm, in the preferred embodiments—from 30 µm to 50 µm.

In the second aspect of the invention, a tissue spheroid 3D printing device is proposed, including a printhead as described hereabove;

feeder for tissue spheroids with nutrient medium into the inlet channel;

at least one appliance for the removal of nutrient medium connected to the upper and/or lower nutrient medium separation channels of the printhead, supporting piston, configured to insert the supporting piston into the channel and move within it until the printhead output channel is closed, printing tool configured to feed the printhead into the outlet channel through the upper entrance port;

tissue spheroid position detection system in the outlet channel of the printhead (hereinafter the position detection system);

a computer device for controlling the feeder of tissue spheroids with nutrient medium, for controlling the registration system, for controlling the movement of the supporting piston and printing tool, and for controlling the nutrient medium disposal.

In some embodiments of the second aspect of the invention, printhead is replaceable.

In some embodiments of the second aspect of the invention, the feeder device includes a means of controlling the pressure in the nutrient medium container to produce the pulsations necessary to move tissue spheroids from the loading container into the inlet channel of the printhead.

The increase in printing speed is achieved by automating the process and applying the kinematic scheme of the device using a smaller number of moving elements (pistons) and, as a consequence, reducing the number of stages compared to the closest analogue, in which the printing speed is limited by the speed of the three stages.

The quality of bioprinting is achieved thanks to the function of removing the nutrient medium from the mixture—tissue spheroids, which is fed by the feeder into the inlet channel. This function is realized by the design of the channel system in the printhead. In particular, the function is implemented by the presence of 2 microchannel systems (at the upper and lower separation channels), connected on one side with the outlet channel of the printhead respectively in the first area of the outlet channel and in the second area of the outlet channel, and on the other—with the corresponding separation channel. The size of each microchannel in the microchannel system is such that prevents tissue spheroids from entering the separation channels. Nutrient medium is pumped into a container of nutrient medium removal configured to collect used nutrient medium. Nutrient medium separation prevents the undesirable formation of nutrient medium droplets at the printhead's outlet channel. Since the nutrient medium does not come out of the printhead's outlet channel, each spheroid is precisely positioned on the printed surface during printing (spheroids do not move within the fluid).

Increasing the speed and quality of bioprinting with single tissue spheroids makes it possible to perform bioprinting of functional organ constructs both in vitro, and in vivo.

In order to ensure that only one spheroid is outputted to the substrate, the plunger and the printing instrument operate alternately, and the geometry of the curvilinear inlet channels in the printhead is used. The location of spheroids one-by-one in the inlet channel allows delivering them to the substrate undamaged, which helps improve the quality of bioprinting.

Since the diameter of the channels, including the diameter of the inlet and outlet channels, can be selected at will, the optimum diameter of the channels can be selected according to the required diameter of tissue spheroids, chosen in the range from 290 µm to 400 µm. This size is optimal for the preservation of the highest percentage of live cells in a spheroid.

BRIEF DESCRIPTION OF DRAWINGS

The features of the invention will become more obvious on the basis of the following detailed description, which makes reference to the appended drawings, in which.

DETAILED DESCRIPTION OF THE EMBODIMENTS OF THE INVENTION

Figure 1:
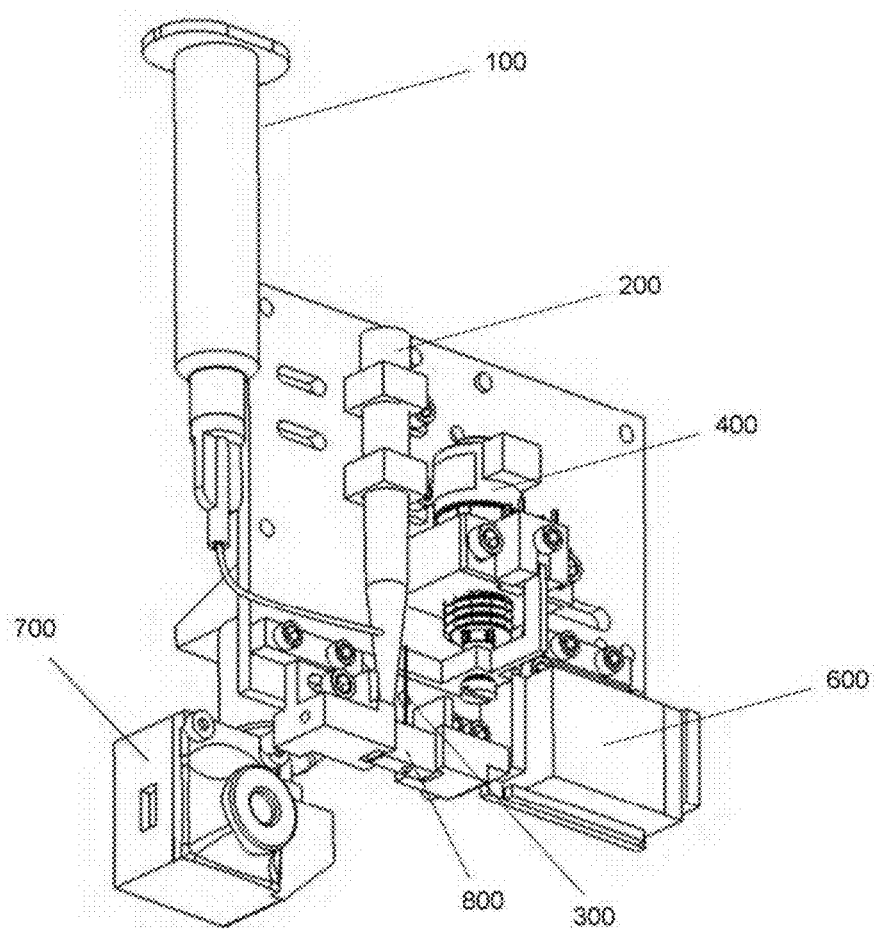
FIG. 1 shows a general view of one particular embodiment of the proposed tissue spheroidal printing device.

Definitions of some terms used in this description are given below. Unless specified otherwise, technical and scientific terms in this application have standard meanings, generally accepted in the scientific and technical literature.

In this context, the term "tissue spheroids" (or "spheroids") refers to tissue spheroids that can be created from different cell types. For example, spheroids may consist, without limitation, of fibroblasts, chondrocytes, keratinocytes, primary astrocytes, thyrocytes, MMSCs (multipotent mesenchymal stromal cells), and tumor line cells (e.g., human melanoma cells). In some embodiments of the invention, the printhead may be used for simultaneous printing with different types of tissue spheroids (i.e., consisting of different types of cells), for which purpose the printhead must contain several inlet channels, each of which is used for one type of spheroids. In different embodiments of the invention, the proposed printhead can be made configured to print with tissue spheroids of any diameter, however in most preferable embodiments, not limiting the scope of this invention, diameter of spheroids is chosen in the range from 290 μm to 400 μm. This size is optimal for the preservation of the highest percentage of live cells in a spheroid.

In this context, the term "nutrient medium" refers to any nutrient medium chosen according to the type of cells used to create tissue spheroids. For example, alpha-MEM medium for keratinocyte tissue spheroids, primary astrocytes and human melanoma cells can be used as a nutrient medium. DMEM medium for tissue spheroids from fibroblasts, chondrocytes, MMSCs, and tumor line cells can be used as a nutrient medium. F-12 medium can be used as a nutrient medium for tissue spheroids made of thyrocytes, ovarian cultures of Chinese hamster cells and hybridoma cells. RPMI-1640 medium can be used as a nutrient medium for tissue spheroids from lymphoid cells. DMEM/F12 medium can be used as a nutrient medium for tissue spheroids from pancreatic gland cells.

If necessary, agents facilitating the bonding of spheroids after they are printed on the substrate can be dissolved in the nutrient medium.

In this description and in the claims, the terms "includes," "having," "provided with," "containing" and their other grammatical forms are not intended to be interpreted in an exceptional sense, but, on the contrary, are used in a non-exclusive sense (that is, in the sense of "being composed of").

Only expressions such as "consisting of" should be considered as exhaustive.

In addition, the terms "first," "second," "third," etc. are used simply as conditional markers, without imposing any numerical or other restrictions on the listed objects.

The term "connected" means functionally connected, and any number or combination of intermediate elements between the components to be connected (including the absence of intermediate elements) may be used.

In one of its aspects, this invention relates to a device designed for 3D printing with tissue spheroids in combination with any 3D positioning system. Structural design of such device is illustrated in Fig. For the automated operation of the device, filled with suspension with tissue spheroids (i.e. tissue spheroids with a nutrient medium), the following elements are necessary: container for nutrient medium 100, container for tissue spheroid loading 200, printing tool 300 and the drive element 400 for motorizing the movement of the printing tool 300, the supporting plunger 500 (not shown in FIG. 1) and solenoid 600, designed to motorize the movement of the prop plunger 500, digital camera 700. The main element of the device is the printhead 800, which includes an orifice for the output of tissue spheroids and at least one orifice for receiving the material fed into the printhead (tissue spheroids with nutrient medium).

Containers for storage of material: a container for loading tissue spheroids 200 and a container for nutrient medium 100—can be of any design. In the illustrated embodiment, the containers have cylindrical form bevel one end. The capacity of the container for tissue spheroids 200 is smaller than that of the nutrient medium container 100.

In order to provide bioprinting with tissue spheroids while maintaining their viability, the spheroids must be kept in nutrient medium before printing. For this purpose, containers 100 and 200 are connected by a hydraulic line arranged as communicating vessels for replenishing the container for loading tissue spheroids with nutrient medium. The container for loading tissue spheroids 200 can be connected to the printhead 800 directly ("tight fit") and/or via flexible hydraulic lines.

In the shown embodiment, the container for loading tissue spheroids 200 is mechanically tightly connected with printhead 800. The connection of the tissue spheroid loading container 200 with the printhead's material inlet port 800 (i.e. the entrance port of the inlet channel) shown in FIG. 1 is a "tight fit" connection. The tightness of the connection is ensured by tight insertion of the bevel end of container 200 into the cylindrical opening of the inlet channel of the printhead 800. When tissue spheroids are loaded into container 200, they, by the force of gravity, move into the inlet channel of the printhead 800 through the feed receiving port (entrance port of the inlet channel). In many cases, tissue spheroids "stick" to the inner surface of the loading container clogging the passage into the printhead's inlet channel.

To resolve this problem, the device is additionally equipped with a means for controlling the pressure in the nutrient medium container (not shown in FIG. 1) to generate pulsations necessary to get tissue spheroids moving into the printhead's inlet channel. The means of pressure control has a connection with the nutrient medium container either directly and/or through flexible hydraulic lines.

The means of pressure control is a means that generates force to ensure the movement of the feed material. The pressure generated in the nutrient medium container 100 pushes the mixture of tissue spheroids and nutrient medium into the printhead's material inlet port 800.

In one of the embodiments, said pressure control means can be a pump unit capable of generating pressure drops, such as pulsations, required to get tissue spheroids moving into the printhead while mixing them in the container.

Printhead 800 is equipped with a printing tool 300. In one embodiment the printing tool 300 is mechanically coupled to the drive element 400, which can be executed on the basis of a stepper motor with a linear actuator. In different embodiments of the invention, any other means of driving printing tool can be used that ensure reciprocating movement of the printing tool 300.

For example, a piezoelectric motor, a pneumatic motor, an electric motor, a hydraulic motor or any other functionally similar device known from the art.

The printhead 800 also includes a supporting piston 500, mechanically connected to the solenoid piston 600, which ensures reciprocating movement of said supporting piston 500. The supporting piston 500 is required for closing the spheroid outlet channel, which allows for only a single spheroid to be printed (i.e. ensures printing with single tissue spheroids).

To determine spheroid's position, a spheroid position recording system is provided in the printhead 800. Such recording system can be a digital camera 700. In this case, the image quality obtained from the camera 700 must satisfy the following condition: the number of pixels per spheroid—at least 10 PCs. The camera 700 is positioned in front of the printhead 800 so as to be able to get a front shot of the printhead 800.

Figure 2:
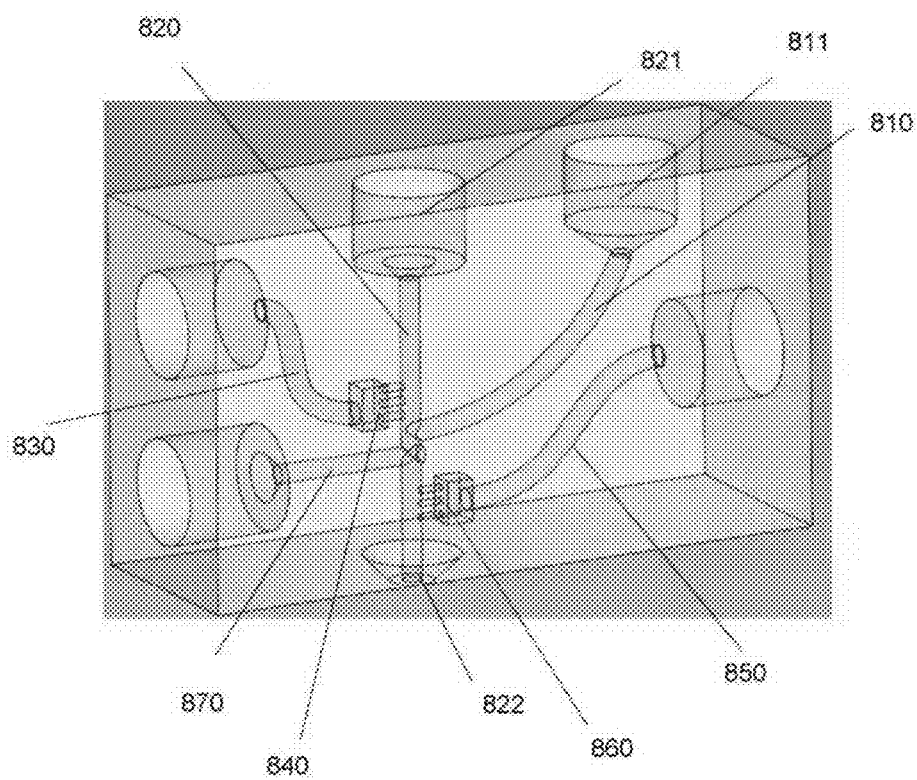
FIG. 2 is a schematic view of one particular embodiment of the printhead, which is part of the proposed tissue spheroidal printing device.

The device's principal element is the printhead 800, which is also one of the aspects of this invention. It is within the printhead where spheroids are moved forward and registered, where the nutrient medium is separated and finally spheroids are placed onto the substrate. FIG. 2 depicts a schematic view of the printhead 800 used in the tissue spheroid printer.

The printhead 800 can be manufactured using, for example, the known micro-jet molding technique (e.g. casting, imprinting or injection molding). Alternatively, commercially available 3D printing technology can be used for manufacturing the printhead.

In some embodiments of the invention, the printhead is disposable. Using a disposable printhead can reduce the risk of contamination of the materials used for different printing jobs. In some embodiments of the invention, the printhead can be changeable and selected to match the size of the tissue spheroids used.

The printhead is a solid body with channels inside. In the illustrated embodiment of the invention, the channels have cylindrical form. However, the printhead described in this document may also contain other channel shapes in addition to the cylindrical ones.

The solid material of which the printhead is made may be transparent in some embodiments of the invention. For example, the material can be selected from glass, polycarbonate, acrylic, polydimethylsiloxane.

As already mentioned, in the preferred embodiments of the invention printhead has channels that allow using spheroids with diameters ranging from 290-400 µm, the optimal diameter of spheroids for bioprinting from the viewpoint of printing performance and viability of spheroids lies within 290-300 µm. The diameter of the spheroids that can be used in a particular printhead according to the invention depends on the diameter input and output channels (the diameter of the channels should be greater than the diameter of the spheroids by 30±10 microns). If desired, printhead of a different size can be used.

In the embodiment illustrated in FIG. 2, the printhead 800 includes the inlet channel 810 for receiving and directing the supply of printing material (nutrient medium with tissue spheroids), the outlet channel 820, the upper channel 830 for the separation of nutrient medium with a system of microchannels 840, the lower channel 850 for the separation of nutrient medium with a system of microchannels 860, and the channel for the supporting piston 870.

In some embodiments of the invention, there may be several inlet channels connected to appropriate containers for loading tissue spheroids. In this case, the inlet channel system additionally includes a system of valves/plungers so that only one spheroid could be fed from different inlet channels into the outlet channel. However, this is not the subject matter of this invention.

In the manufacture of the printhead 800, the diameter of the inlet channel 810 is selected depending on the diameter of the tissue spheroids so that spheroids could move through the channel only one at a time. The diameter of the printhead's outlet channel is selected so that it is not narrower than the inlet channel.

Each channel has its inlet and outlet. The inlet channel 810 has curvilinear form for the purpose of better feed of spheroids into the printhead (conversion from horizontal to vertical channel orientation). The inlet channel 810 is connected to the material reception port 811, which allows tissue spheroids with nutrient medium to pass from tissue spheroid loading container 200 to the corresponding inlet channel 810 of the printhead 800. The printhead's outlet channel 820 is connected to the upper entrance port 821 into which the print tool 300 is inserted, and to the lower exit port 822 from which single tissue spheroids are outputted to the substrate (not shown in FIG. 2). Inlet channel 810 and outlet channel 820 intersect at the first point.

In the illustrated embodiment of the invention the upper separation channel 830 and the lower separation channel 850 have curvilinear form and are connected on one side to the device for the removal of the nutrient medium (not shown in FIG. 2), and on the other side—to the outlet channel 820 through the system of microchannels 840,860. In other embodiments of printhead according to the invention, separation channels may have another form. Moreover, in some embodiments, one channel may be curvilinear, while the other is rectilinear. Each of the separation channels 830, 850 is connected to the lower microchannel system and the upper microchannel system, respectively. In the shown embodiment of the print head (FIG. 2) a microchannel system consisting of three microchannels is selected. However, in other printhead designs in accordance with the invention, the number of microchannels included in the microchannel system may be one, two, three or more.

The upper microchannel system 840 is connected with the outlet channel 820 in the first area of the outlet channel. The lower microchannel system 850 is connected with the outlet channel 820 in the second area of the outlet channel. The configuration of connections and intersections of the channels in the printhead 800 is such that the first point of intersection of the inlet channel 810 and outlet channel 820 is located between the first area and the second area of intersection of the separation channels through the corresponding systems of microchannels and the outlet channel.

The system of microchannels is embedded in the printhead body. The diameter of each microchannel is narrower than that of the separation channels and is selected depending on the diameter of the tissue spheroids used for printing so that the spheroids could not move through the microchannel. The diameter of a microchannel does not exceed 200 µm and ranges from 10-150 µm. The choice of channel diameter depends on their number. The more is the number of channels, the narrower is the diameter of each one of them. For example, in the embodiment where the printhead includes five microchannels and tissue spheroids 290 µm in diameter are used, the diameter of the separation channels is 300 µm and the diameter of each microchannel is 30 µm.

If the microchannel system consists of one microchannel, then, given the same configuration of separation channels and the use of tissue spheroids 300 µm in diameter, the diameter of a microchannel will be 150 µm.

The system of microchannels is needed for the separation of nutrient medium (without spheroid separation) without increasing the channel's flow friction.

A nutrient medium removal apparatus connected to the separation channels can be a manually and/or automatically controlled syringe or a pumping unit capable of generating a pressure drop from −0.5 kg/cm2 up to +0.5 kg/cm2.

In some embodiments according to the present invention to each separation channel: one syringe device or pump device can be connected to the upper separation channel and the lower separation channel.

In some embodiments of this invention, the upper separation channel and the lower separation channel can be connected by a hydraulic line, to which a nutrient medium removal apparatus may be connected.

The supporting piston channel 870 is designed with the possibility of inserting a supporting piston 500 into the printhead. The supporting piston channel 870 intersects with the outlet channel 820 at the second point, which is located between the first point of intersection of the inlet channel 810 with the outlet channel 820 and the second area of intersection of the lower separation channel 850 through the lower microchannel system 860 with the outlet channel 820.

In the illustrated embodiment of the invention, the tissue spheroid printing device includes a computing device with a processor, microcontroller, or other electronic computational means, which hardware and software provide for the possibility of performing the functions described below:

controlling the device for feeding tissue spheroids with nutrient medium to regulate the volume and speed of the material fed into the printhead;

controlling the device for nutrient medium removal;

receiving information from the system of registration, processing of the received images, and locating tissue spheroids based on the received information;

sending controlling signal to the supporting piston solenoid relay to ensure the movement of the supporting piston in the corresponding channel of the printhead depending on the position of tissue spheroid in the printhead's outlet channel;

sending controlling signal to the drive element to ensure the movement of the printing tool in the printhead's outlet channel depending on the position of tissue spheroid in the printhead's outlet channel.

The computing device has a digital input channel that receives digital signals from the registration system, a digital input channel for initiating single-spheroid printing process, digital outputs for sending signals to the actuating member and solenoid relay to ensure the movement of the printing tool and the supporting piston, respectively.

In one of the embodiments of the invention, all elements of the single tissue spheroid printing device are located on a single platform and are mechanically connected to each other. Possible embodiments of the invention include, for example, an embodiment where the computing device is located at some distance from the printing device.

In addition, the computing device can be connected to an external computing device to initiate the operation of the printhead, which can be performed on the basis of a wide range of electronic computing devices, for example, a personal computer, laptop, server cluster, smartphone, etc.

When connected to an external computing device, the print head computing device receives a signal to start the printhead operation cycle (described below), then the print head computing device starts the printhead systems, according to the algorithm laid down in it.

The computing device processes the images sent by the registration system. When a spheroid is positioned between the printing tool and the supporting piston, the processor sends signals to initiate movement of the supporting piston and the printing tool, according to the algorithm described below in the description of one cycle of operation.

In order to prepare the device for operation it is necessary to load the nutrient medium supply container with nutrient medium and To load tissue spheroids into the tissue spheroids container.

Figure 3:
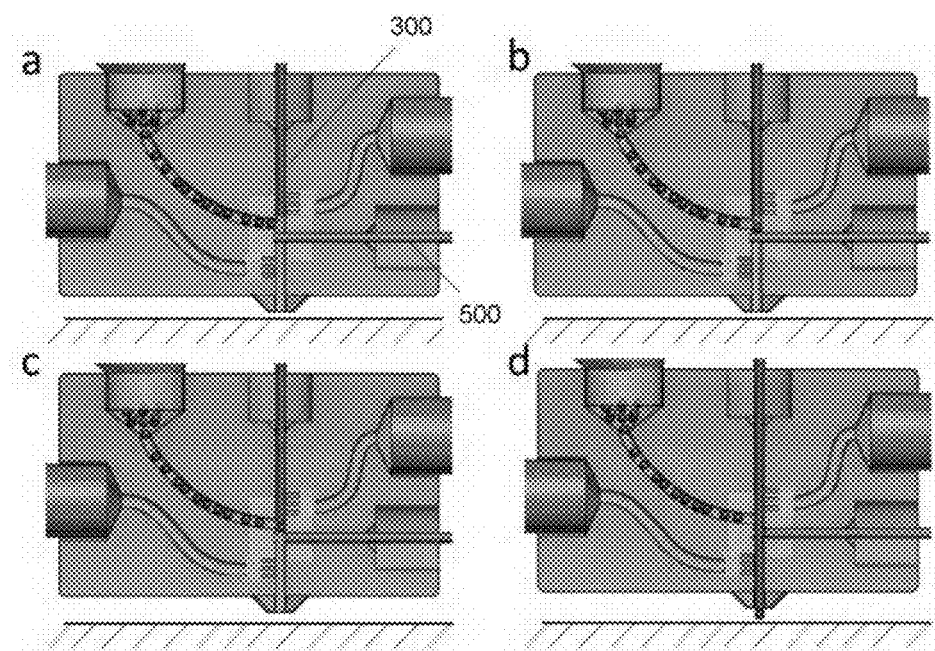
FIG. 3 is a process diagram of one particular embodiment of the tissue spheroid printer with printhead according to the invention.

A work cycle of printhead by phases is illustrated in FIG. 3 To initiate the movement of tissue spheroids in the printhead's inlet channel 810, a negative pressure is created in the upper 830 and lower 850 separation channels by means of a syringe pump or other vacuuming unit. As a result, the nutrient medium is pumped through the upper 830 and lower 850 microchannel systems into the spent medium collection container (not shown conventionally in FIG. 1-3) (the size of the microchannels does not allow tissue spheroids to pass into the separation channels). Separation of the nutrient medium will neutralize the negative exit from droplets of nutrient medium from the output channel 820 printhead, thereby providing movement of the spheroids into the input channel 810 printhead (FIG. 3a) from the spheroid loading vessel 200 and the spheroid movement in the input channel 810 to the output channel 820 of the printhead.

Once the digital camera 700 has detected the position of a tissue spheroid (FIG. 3b, reference number 1) (between the supporting piston and the printing tool (FIG. 3b, reference number 2)), the supporting piston 500 (FIG. 3c, reference number 3)) pulls aside opening the way for the movement of the printing tool 300, as shown in FIG. 3c; then the printing tool 300 performs the printing of the spheroid, i.e. moves the spheroid until contact with the substrate surface onto which the printing is performed (FIG. 3d, reference number 4). After execution of the printout the printing tool 300 rises to a position below the starting position by the spheroid diameter so that the supporting piston 500 could return to its starting position without allowing the next spheroids to slide into the outlet channel 820. Then the printing tool 300 rises to its starting position. This is the end of the work cycle.

The described technological solution allows high speed printing with single tissue spheroids onto biocompatible materials (collagen, fibrinogen, electrospinning matrix, etc.).

The use of this device with the "turnstile" system for spheroid printing allows bioprinting with single tissue spheroids onto layered structures or grids made of biocompatible material.

The above description was given for different embodiments or implementations of this invention.

It has to be understood that such embodiments can be subject to numerous and varied modifications and changes by a person skilled in this field without deviating from the nature of the invention, which is determined solely by the claims attached. Thus, for example, the structural element of the device mentioned here in singular should be understood as not excluding the possibility of multiple elements, unless such an exception is explicitly stated or implied in the context. References to the "embodiment" or "implementation" should not be construed as precluding the existence of other embodiments, which also include the specified features Furthermore, unless explicitly stated otherwise, embodiments "including", "containing" or "having" a certain element or set of elements with some particular characteristic or feature may include additional elements, regardless of whether they possess that characteristic or feature.

It should also be noted that the specific layout of the printhead components and the printing device using the printhead (e.g., their number, types, placement, etc.) in the illustrated embodiments of the invention can be changed to other variants in other embodiments. Different embodiments may use different quantities of certain modules or blocks, different type or types of certain modules or blocks, a certain module or block may be added, or a certain module or block may be excluded.

It should be clearly understood that the above description is only intended to illustrate this invention, not to limit the scope of its copyright protection. For example, the above embodiments (and/or their features) can be used in any combination with each other. In addition, numerous modifications can be made to adapt one particular embodiment to the features of various other embodiments without deviating from the scope of protected copyright of the invention. The sizes, types, orientations, number and positions of various structural elements described herein are intended to characterize parameters of embodiments considered preferable nowadays and are in any case not limiting, but only illustrative embodiments. After considering the above description, it will be obvious to a person skilled in the art that many other options and modifications of the invention are possible within the scope and nature of the protected copyright. Consequently, the scope of protection should be determined taking into account only the claims, together with the full range of equivalents covered by the claims.

We claim:

1. A printhead for use in a tissue spheroidal printer, including
   a system of channels, including:
   at least one inlet channel, which diameter is selected according to the diameter of the tissue spheroids used for printing so that the spheroids can only move one at a time through the channel, for receiving and directing the supply of nutrient medium with tissue spheroids,
   an output channel which diameter is selected to be at least as large as the input channel diameter, with the top print tool inlet and the bottom outlet for the output of tissue spheroids,
   the upper channel of separation of the nutrient medium and the lower channel of separation of the nutrient medium, each of which connects the device for removal of the nutrient medium to the output channel through a system of microchannels: accordingly, the upper separation channel of the nutrient medium is in the first region of the output channel, and the lower separation channel of the nutrient medium is in the second region of the output channel,
   a channel for the supporting piston, configured to insert a supporting piston,
   the channels are configured as follows:
   the input channel is connected to the output channel at the first point of intersection located between the first area of the output channel and the second area of the output channel, and the supporting piston channel is connected to the output channel at the second intersection point located between the first intersection point and the second area of the output channel,
   and the diameter of each microchannel of the microchannel system is selected according to the diameter of the tissue spheroids used for printing so that the spheroids cannot move through the microchannel.

2. The printhead according to claim 1 is described as it contains a plurality of input channels, wherein the diameter of all input channels is the same and all input channels are connected to the output channel.

3. The printhead according to claim 1 characterized in that one or more input channels for receiving and directing nutrient medium with tissue spheroids have curvilinear form.

4. The printhead according to claim 1, characterized in that the channels are located inside a bulky body.

5. The printhead according to claim 3, characterized in that the bulky body is made of a solid transparent material.

6. The printhead according to claim 1, characterized in that the diameter of tissue spheroids used is within the range of 290 µm-400 µm, and the diameter of the input and output channels is by 30 µm±10 µm larger than the diameter of the used tissue spheroids.

7. The printhead according to claim 5, characterized in that the diameter of each microchannel of the microchannel system is from 10 µm to 200 µm.

8. A tissue spheroid printing device, including:
   the printhead according to any of the claims 1-7,
   feeder for tissue spheroids with nutrient medium into the inlet channel of the printhead,
   at least one appliance for the removal of nutrient medium connected to the upper and/or lower nutrient medium separation channels of the printhead,
   the supporting piston, configured to insert the supporting piston into the channel and move within it until the printhead output channel is closed,
   printing tool configured to feed the printhead into the outlet channel through the upper entrance port;
   tissue spheroid position detection system in the output channel of the printhead,
   a computer device for controlling the feeder of tissue spheroids with nutrient medium, for controlling the registration system, for controlling the movement of the supporting piston and printing tool, and for controlling the nutrient medium disposal.

9. The device according to claim 8 characterized in that the printhead is replaceable.

10. The device according to claim 7 characterized in that the feeder includes a means of controlling the pressure in the nutrient medium container to produce the pulsations necessary to move tissue spheroids from the loading container into the inlet channel of the printhead.

* * * * *